(12) United States Patent
Hamauzu

(10) Patent No.: US 12,039,005 B2
(45) Date of Patent: Jul. 16, 2024

(54) LEARNING DEVICE, LEARNING METHOD, LEARNING PROGRAM, TRAINED MODEL, RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Shin Hamauzu, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 363 days.

(21) Appl. No.: 17/469,618

(22) Filed: Sep. 8, 2021

(65) Prior Publication Data
US 2022/0083812 A1    Mar. 17, 2022

(30) Foreign Application Priority Data

Sep. 15, 2020   (JP) .................................. 2020-154638

(51) Int. Cl.
*A61B 6/12*    (2006.01)
*A61B 6/46*    (2024.01)
(Continued)

(52) U.S. Cl.
CPC .............. *G06F 18/214* (2023.01); *A61B 6/12* (2013.01); *A61B 6/463* (2013.01); *G06T 7/0012* (2013.01); *G06V 10/22* (2022.01); *G16H 30/40* (2018.01); *G16H 50/20* (2018.01); *G06T 2207/10116* (2013.01); *G06T 2207/20081* (2013.01);
(Continued)

(58) Field of Classification Search
CPC ......... G06F 18/214; A61B 6/12; A61B 6/463; G06T 7/0012; G06T 2207/10116; G06T 2207/20081; G06T 2207/30004; G06T 2207/20084; G06T 7/73; G06V 10/22; G06V 2201/034; G06V 10/255;
(Continued)

(56) References Cited

U.S. PATENT DOCUMENTS

| | | | |
|---|---|---|---|
| 9,317,920 B2 * | 4/2016 | Gluncic | ............... A61B 8/5215 |
| 9,767,554 B2 * | 9/2017 | Chou | ........................ G06T 7/11 |

(Continued)

FOREIGN PATENT DOCUMENTS

| | | |
|---|---|---|
| JP | 2010-131371 A | 6/2010 |
| JP | 2011-218089 A | 11/2011 |

(Continued)

OTHER PUBLICATIONS

Author Unknown, "ThreadX® XRD Packing Gauze—Sentry Medical", retrieved from The Wayback Machine—"https://web.archive.org/web/20190322030016/https://www.sentrymedical.com.au/product/threadx-xrd-packing-gauze/", archive date of Mar. 22, 2019 (Year: 2019).*

(Continued)

*Primary Examiner* — Aaron W Carter
(74) *Attorney, Agent, or Firm* — Studebaker & Brackett PC

(57) ABSTRACT

A processor performs machine learning, which independently uses, as training data, each of a plurality of radiographic images that do not include a surgical tool and a plurality of surgical tool images that include the surgical tool and have image quality corresponding to images acquired by radiography, to construct a trained model for detecting a region of the surgical tool from an input radiographic image.

12 Claims, 7 Drawing Sheets

(51) Int. Cl.
    *G06F 18/214*     (2023.01)
    *G06T 7/00*     (2017.01)
    *G06V 10/22*     (2022.01)
    *G16H 30/40*     (2018.01)
    *G16H 50/20*     (2018.01)

(52) U.S. Cl.
    CPC ............... *G06T 2207/30004* (2013.01); *G06V 2201/034* (2022.01)

(58) Field of Classification Search
    CPC ........ G06V 10/82; G16H 30/40; G16H 50/20; G16H 20/40; G16H 30/20; G16H 50/70
    See application file for complete search history.

(56) References Cited

U.S. PATENT DOCUMENTS

| | | | |
|---|---|---|---|
| 9,792,682 B2* | 10/2017 | Gluncic | G16H 30/40 |
| 10,839,514 B2* | 11/2020 | Accomazzi | G16H 30/40 |
| 11,488,304 B2* | 11/2022 | Katayama | G06F 18/214 |
| 11,972,559 B2* | 4/2024 | Hamauzu | A61B 17/29 |
| 2010/0104167 A1 | 4/2010 | Sakaguchi et al. | |
| 2013/0136323 A1 | 5/2013 | Asiyanbola et al. | |
| 2014/0328517 A1* | 11/2014 | Gluncic | G06T 7/0014 382/103 |
| 2014/0334709 A1* | 11/2014 | Siewerdsen | G06T 7/32 382/132 |
| 2016/0066877 A1* | 3/2016 | Gluncic | G16H 40/67 600/424 |
| 2016/0071264 A1* | 3/2016 | Agam | G06V 10/774 382/128 |
| 2017/0069081 A1* | 3/2017 | Gluncic | G16H 30/40 |
| 2017/0143284 A1* | 5/2017 | Sehnert | A61B 6/5258 |
| 2018/0279913 A1* | 10/2018 | Frasier | A61B 34/20 |
| 2019/0311794 A1* | 10/2019 | Abe | G16H 40/63 |
| 2021/0015440 A1* | 1/2021 | Hamauzu | A61B 6/5205 |
| 2021/0063323 A1 | 3/2021 | Nakatani et al. | |
| 2021/0085267 A1* | 3/2021 | Hamauzu | A61B 6/5217 |
| 2021/0093280 A1* | 4/2021 | Hamauzu | H05G 1/44 |
| 2021/0104038 A1* | 4/2021 | Parsons | G06T 7/62 |
| 2021/0241039 A1* | 8/2021 | Hamauzu | G06V 10/764 |
| 2021/0244370 A1* | 8/2021 | Hamauzu | A61B 6/12 |
| 2021/0251583 A1* | 8/2021 | Hamauzu | A61B 17/3201 |
| 2022/0083805 A1* | 3/2022 | Hamauzu | G06T 7/0012 |
| 2022/0083812 A1* | 3/2022 | Hamauzu | G16H 30/40 |
| 2022/0113263 A1* | 4/2022 | Hosomi | A61B 6/465 |
| 2022/0114729 A1* | 4/2022 | Hu | A61B 6/12 |
| 2022/0318998 A1* | 10/2022 | Fukuda | G06T 7/0012 |
| 2022/0383564 A1* | 12/2022 | Koike | G06T 11/006 |
| 2023/0094397 A1* | 3/2023 | Machii | A61B 6/5223 382/131 |
| 2023/0096694 A1* | 3/2023 | Takahashi | G06T 5/50 382/132 |
| 2023/0097849 A1* | 3/2023 | Takahashi | G06V 10/70 382/131 |
| 2023/0098859 A1* | 3/2023 | Kitamura | A61B 5/00 600/118 |

FOREIGN PATENT DOCUMENTS

| | | |
|---|---|---|
| JP | 2017-185007 A | 10/2017 |
| JP | 2018-068863 A | 5/2018 |
| WO | 2019/159440 A1 | 8/2019 |

OTHER PUBLICATIONS

"New function of Fujifilm, a very lightweight mobile digital X-ray device, and a "function of recognition of surgical gauze by using AI technology", and contribute to the confirmation of the residual residues in the human body after the new release of the JAtechnology"; and contribute to the prevention of overlooking", Apr. 2, 2020, innavi net, URL <https://www.innervision.co.jp/sp/products/release/20200521>.

An Office Action mailed by the Japan Patent Office on Jul. 4, 2023, which corresponds to Japanese Patent Application No. 2020-154638, and is related to U.S. Appl. No. 17/469,618; with English translation.

* cited by examiner

LEARNING DEVICE, LEARNING METHOD, LEARNING PROGRAM, TRAINED MODEL, RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-154638 filed on Sep. 15, 2020. The above application is hereby expressly incorporated by reference, in its entirety, into the present application.

BACKGROUND

Technical Field

The present disclosure relates to a learning device, a learning method, a learning program, a trained model, a radiographic image processing device, a radiographic image processing method, and a radiographic image processing program.

RELATED ART

Various surgical tools, such as gauze to suppress bleeding, a thread and a suture needle for sewing up a wound or an incision, a scalpel and scissors for incision, a drain for draining blood, and forceps for opening an incision, are used in a case in which a surgical operation is performed for a patient. The surgical tools may cause serious complications in a case in which they remain in the body of the patient after surgery. Therefore, it is necessary to check that no surgical tools remain in the body of the patient after surgery.

Therefore, a method has been proposed which prepares a trained model that has learned the characteristics of a gauze image using machine learning as a discriminator and inputs an image acquired by capturing a surgical field with a camera to a discriminator to discriminate whether or not gauze is present (see JP2018-068863A).

In addition, a method has been proposed which uses an image portion obtained by cutting out a peripheral region including an object, such as a stent, from a radiographic image as a correct answer image of the object and detects the object from the radiographic image using image recognition with a discriminator that has been trained using the correct answer image and an incorrect answer image other than the object as training data (see JP2017-185007A).

However, since gauze is stained with blood, it is difficult to find gauze in the image acquired by the camera even in a case in which the discriminator is used. Further, a small surgical tool, such as a suture needle, is likely to go between the internal organs. Therefore, it is difficult to find the surgical tool in the image acquired by the camera even in a case in which the discriminator is used. On the other hand, in the method disclosed in JP2017-185007A, the discriminator trained by using the surgical tool, such as gauze, as an object is used, which makes it possible to detect the object from the radiographic image. However, since the radiographic image in which the object remains and which is necessary for training the discriminator is extremely rare, it is difficult to collect a large number of radiographic images in order to train the discriminator. As a result, it is difficult to sufficiently train a learning model that serves as the discriminator.

SUMMARY OF THE INVENTION

The present disclosure has been made in view of the above-mentioned problems, and an object of the present disclosure is to construct a trained model that has been sufficiently trained.

According to an aspect of the present disclosure, there is provided a learning device comprising at least one processor. The processor performs machine learning, which independently uses each of a plurality of radiographic images that do not include a surgical tool and a plurality of surgical tool images that include the surgical tool as training data, to construct a trained model for detecting a region of the surgical tool from an input radiographic image.

In addition, in the learning device according to the aspect of the present disclosure, the surgical tool image may be a radiographic image acquired by performing radiography only on the surgical tool.

Further, in the learning device according to the aspect of the present disclosure, the surgical tool image may be acquired by a method other than the radiography and have an image quality corresponding to an image acquired by the radiography.

Furthermore, in the learning device according to the aspect of the present disclosure, the processor may two-dimensionally project a three-dimensional model of the surgical tool on the basis of a predetermined parameter to derive the surgical tool image.

Moreover, in the learning device according to the aspect of the present disclosure, the processor may set the parameter according to at least one of a contrast of the surgical tool in the surgical tool image, a density of the surgical tool in the surgical tool image, or noise included in the surgical tool image.

In addition, in the learning device according to the aspect of the present disclosure, the surgical tool may include at least one of gauze, a scalpel, scissors, a drain, a suture needle, a thread, or forceps.

In this case, at least a portion of the gauze may include a radiation absorbing thread.

According to another aspect of the present disclosure, there is provided a trained model that is constructed by the learning device according to the present disclosure.

According to another aspect of the present disclosure, there is provided a radiographic image processing device comprising at least one processor. The processor acquires a radiographic image and detects a region of a surgical tool from the radiographic image using a trained model constructed by the learning device according to the present disclosure.

According to yet another aspect of the present disclosure, there is provided a learning method comprising performing machine learning, which independently uses each of a plurality of radiographic images that do not include a surgical tool and a plurality of surgical tool images that include the surgical tool as training data, to construct a trained model for detecting a region of the surgical tool from an input radiographic image.

According to still another aspect of the present disclosure, there is provided a radiographic image processing method comprising: acquiring a radiographic image; and detecting a region of a surgical tool from the radiographic image using a trained model constructed by the learning device according to the present disclosure.

In addition, programs that cause a computer to perform the learning method and the radiographic image processing method according to the present disclosure may be provided.

According to the present disclosure, it is possible to construct a trained model that has been sufficiently trained.

DETAILED DESCRIPTION

Figure 1:
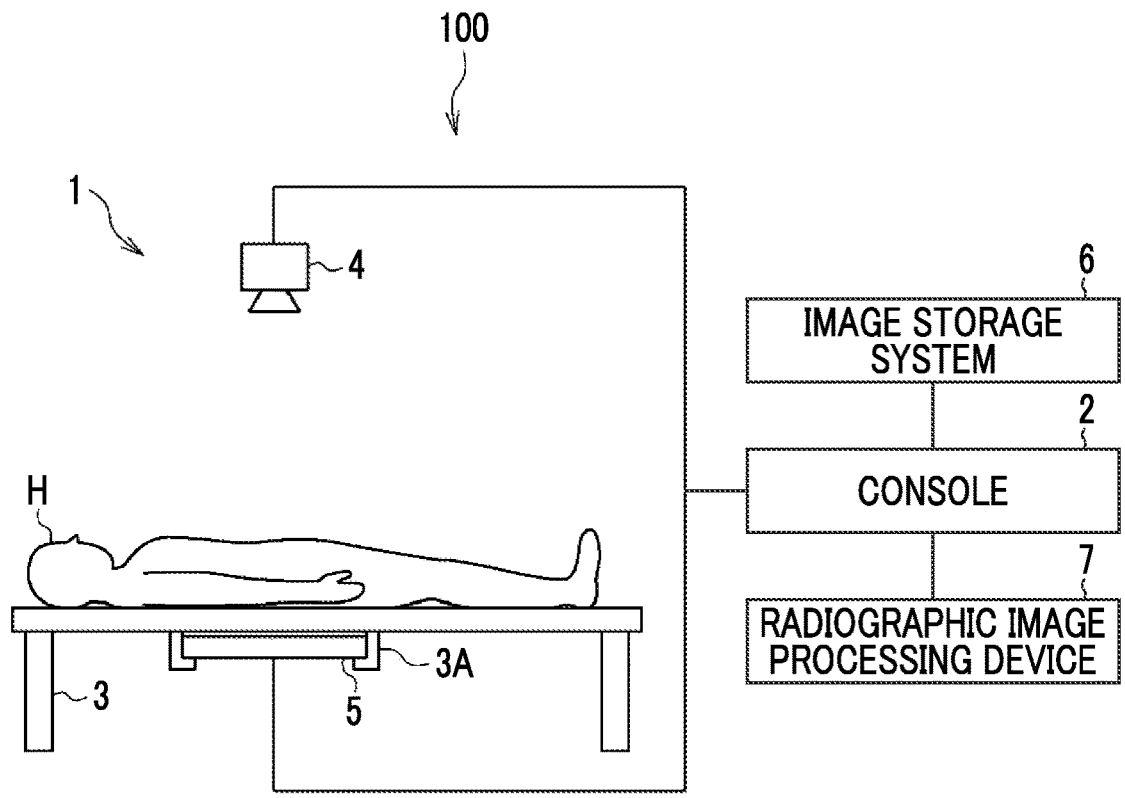
FIG. 1 is a block diagram schematically illustrating a configuration of a radiography system to which a learning device and a radiographic image processing device according to an embodiment of the present disclosure are applied.

Hereinafter, embodiments of the present disclosure will be described with reference to the drawings. FIG. 1 is a block diagram schematically illustrating the configuration of a radiography system to which a learning device and a radiographic image processing device according to an embodiment of the present disclosure are applied. As illustrated in FIG. 1, a radiography system 100 according to this embodiment acquires a radiographic image of a subject that is a patient after a surgical operation and detects a surgical tool included in the radiographic image. The radiography system 100 according to this embodiment comprises an imaging apparatus 1, a console 2, an image storage system 6, and a radiographic image processing device 7.

The imaging apparatus 1 detects radiation, which has been emitted from a radiation source 4, such as an X-ray source, and transmitted through a subject H, with a radiation detector 5 to acquire a radiographic image of the subject H that lies supine on an operating table 3. The radiographic image is input to the console 2.

Further, the radiation detector 5 is a portable radiation detector and is attached to the operating table 3 by an attachment portion 3A that is provided in the operating table 3. In addition, the radiation detector 5 may be fixed to the operating table 3.

The console 2 has a function of controlling the imaging apparatus 1 using, for example, an imaging order and various kinds of information acquired from a radiology information system (RIS) (not illustrated) or the like through a network, such as a wireless communication local area network (LAN), and commands or the like directly issued by an engineer or the like. For example, in this embodiment, a server computer is used as the console 2.

The image storage system 6 is a system that stores image data of the radiographic images captured by the imaging apparatus 1. The image storage system 6 extracts an image corresponding to a request from, for example, the console 2 and the radiographic image processing device 7 from the stored radiographic images and transmits the image to a device that is the source of the request. A specific example of the image storage system 6 is a picture archiving and communication system (PACS).

Next, the radiographic image processing device according to this embodiment will be described. In addition, the radiographic image processing device 7 according to this embodiment includes the learning device according to this embodiment. In the following description, it is assumed that the radiographic image processing device represents the device.

Figure 2:
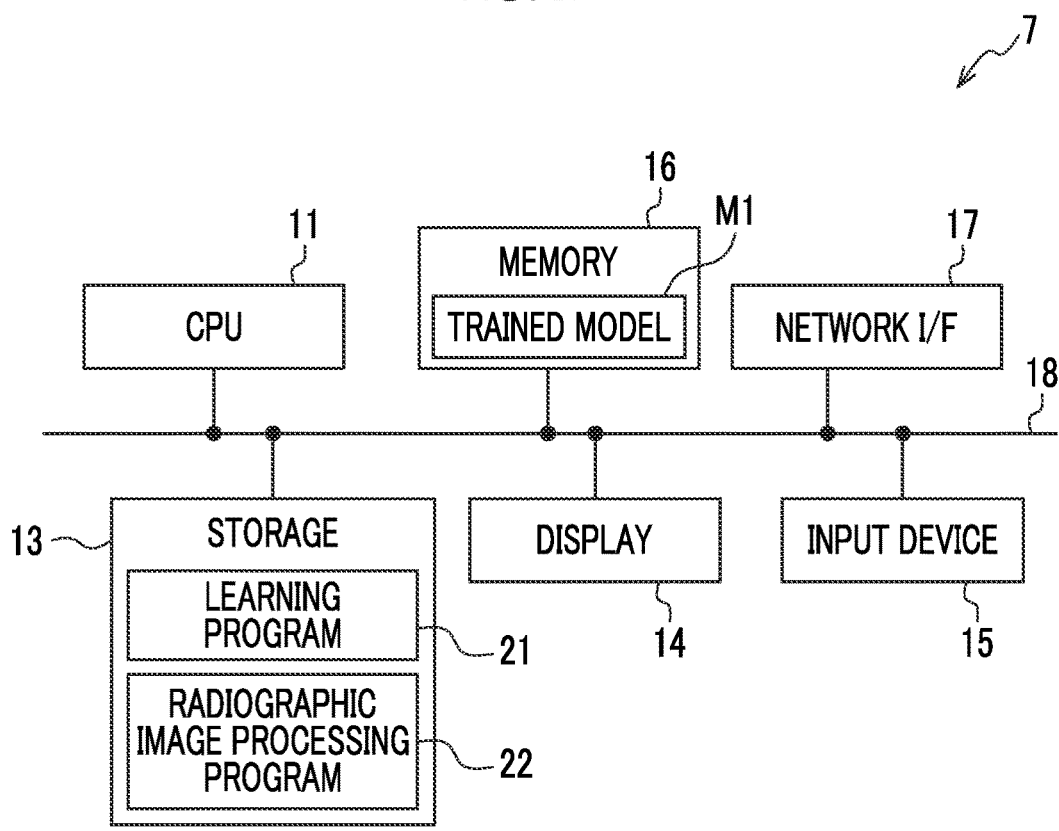
FIG. 2 is a diagram schematically illustrating a configuration of the radiographic image processing device according to this embodiment.

First, the hardware configuration of the radiographic image processing device according to this embodiment will be described with reference to FIG. 2. As illustrated in FIG. 2, the radiographic image processing device 7 is a computer, such as a workstation, a server computer, or a personal computer, and comprises a central processing unit (CPU) 11, a non-volatile storage 13, and a memory 16 as a temporary storage area. In addition, the radiographic image processing device 7 comprises a display 14, such as a liquid crystal display, an input device 15, such as a keyboard and a mouse, and a network interface (I/F) 17 that is connected to a network. The CPU 11, the storage 13, the display 14, the input device 15, the memory 16, and the network I/F 17 are connected to a bus 18. In addition, the CPU 11 is an example of a processor according to the present disclosure.

The storage 13 is implemented by, for example, a hard disk drive (HDD), a solid state drive (SSD), and a flash memory. The storage 13 as a storage medium stores a learning program 21 and a radiographic image processing program 22 which are installed in the radiographic image processing device 7. The CPU 11 reads the learning program 21 and the radiographic image processing program 22 from the storage 13, expands the programs in the memory 16, and executes the expanded learning program 21 and radiographic image processing program 22.

In addition, the learning program 21 and the radiographic image processing program 22 are stored in a storage device of a server computer connected to the network or a network storage so as to be accessed from the outside and are downloaded and installed in the computer forming the radiographic image processing device 7 on demand. Alternatively, the programs are recorded on a recording medium, such as a digital versatile disc (DVD) or a compact disc read only memory (CD-ROM), are distributed and installed in the computer forming the radiographic image processing device 7 from the recording medium.

Figure 3:
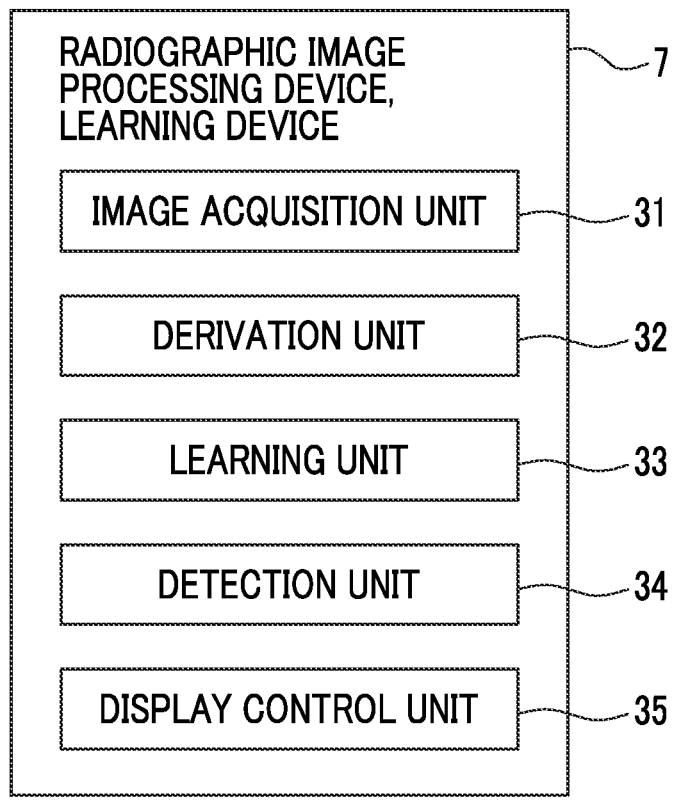
FIG. 3 is a diagram illustrating the functional configuration of the radiographic image processing device according to this embodiment.

Next, the functional configuration of the radiographic image processing device according to this embodiment will be described. FIG. 3 is a diagram illustrating the functional configuration of the radiographic image processing device according to this embodiment. As illustrated in FIG. 3, the radiographic image processing device (learning device) 7 comprises an image acquisition unit 31, a derivation unit 32, a learning unit 33, a detection unit 34, and a display control unit 35. Then, the CPU 11 executes the learning program 21 and the radiographic image processing program 22 to function as the image acquisition unit 31, the derivation unit 32, the learning unit 33, the detection unit 34, and the display control unit 35.

In addition, the image acquisition unit 31, the derivation unit 32, and the learning unit 33 are an example of the learning device according to this embodiment. The image acquisition unit 31, the detection unit 34, and the display control unit 35 are an example of the radiographic image processing device 7 according to this embodiment.

Figure 4:
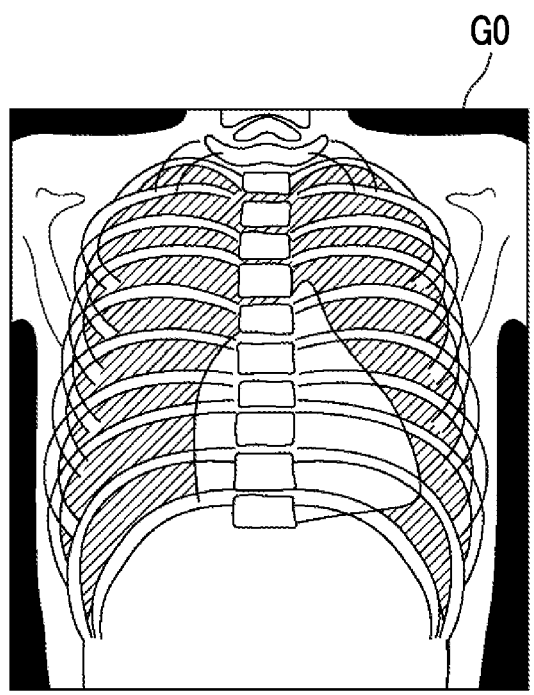
FIG. 4 is a diagram illustrating a radiographic image used as training data.

The image acquisition unit 31 acquires a plurality of radiographic images G0 that do not include the surgical tool as training data for training a learning model M0, which will be described below, from the image storage system 6 through the network I/F 17. FIG. 4 is a diagram illustrating the radiographic image G0. In addition, FIG. 4 illustrates the radiographic image G0 of the chest of the human body as a target part. However, the target part included in the radiographic image G0 is not limited thereto. Further, the image acquisition unit 31 drives the radiation source 4 to irradiate the subject H after surgery with radiation and detects the radiation transmitted through the subject H using the radiation detector 5 to acquire a target radiographic image T0 to be subjected to a surgical tool detection process.

Furthermore, the image acquisition unit 31 also acquires a plurality of surgical tool images E0 indicating the surgical tool as the training data for training the learning model M0 from the image storage system 6. The surgical tool image E0 may be an image acquired by performing radiography on the surgical tool or may be an image acquired by a method other than radiography. In a case in which the surgical tool image E0 is acquired by the method other than radiography, it is preferable that the surgical tool image E0 has image quality corresponding to the radiographic image.

The surgical tool image E0 acquired by the method other than radiography is an image acquired by two-dimensionally projecting a three-dimensional model indicating the surgical tool created by computer graphics or the like using predetermined parameters. The surgical tool image E0 stored in the image storage system 6 may be acquired. However, in this embodiment, a three-dimensional model indicating the surgical tool may be acquired from the image storage system 6, and the derivation unit 32 which will be described below may derive the surgical tool image E0 from the three-dimensional model.

Figure 5:
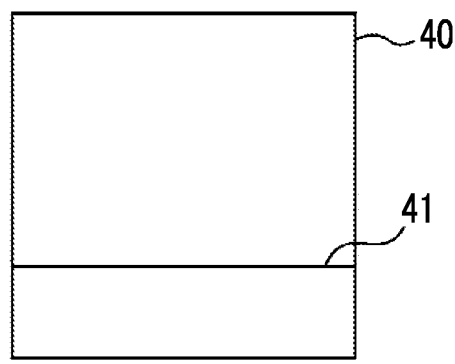
FIG. 5 is a diagram illustrating an image of gauze as a surgical tool.

Here, in this embodiment, it is assumed that gauze is used as the surgical tool. FIG. 5 is a diagram illustrating gauze. As illustrated in FIG. 5, gauze 40 is a plain-woven cotton fabric, and a radiation absorbing thread 41 is woven in a portion of the gauze 40. Cotton yarn transmits radiation, and the radiation absorbing thread 41 absorbs radiation. Therefore, a radiographic image acquired by performing radiography on the gauze 40 includes only the linear radiation absorbing thread 41. Here, during surgery, the gauze 40 is rolled and inserted into the human body in order to absorb blood. Therefore, in a case in which the surgical tool image E0 is acquired by the method other than radiography, the surgical tool image E0 is acquired by two-dimensionally projecting the three-dimensional model in a state in which the gauze is appropriately rolled. In addition, in a case in which the surgical tool image E0 is acquired by radiography, the surgical tool image E0 may be acquired by appropriately rolling the gauze and capturing an image in order to match the aspect in which the gauze 40 is actually used.

Figure 6:
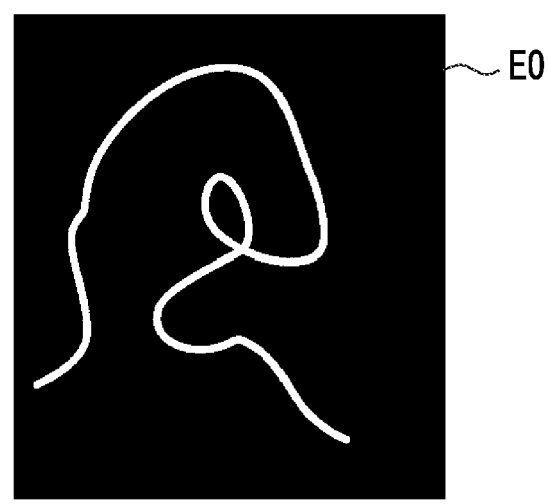
FIG. 6 is a diagram illustrating a surgical tool image used as the training data.

FIG. 6 is a diagram illustrating the surgical tool image E0. A region of the radiation absorbing thread 41 in the surgical tool image E0 corresponds to the amount of attenuation of radiation by the radiation absorbing thread 41. Therefore, in the surgical tool image E0, the radiation absorbing thread 41 included in the gauze 40 has high brightness (low density).

Figure 7:
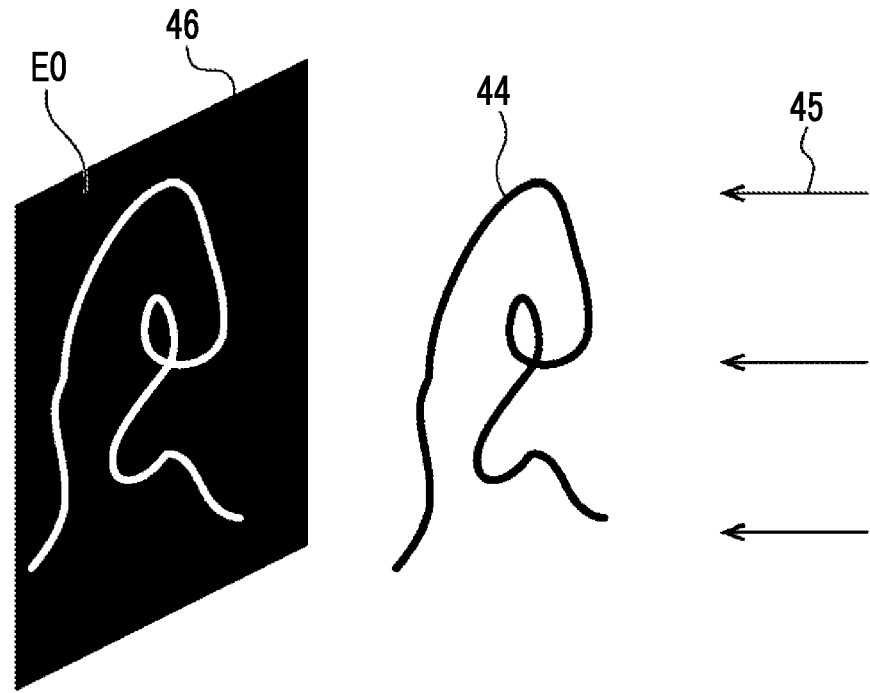
FIG. 7 is a diagram illustrating the derivation of the surgical tool image.

The derivation unit 32 two-dimensionally projects the three-dimensional model of the surgical tool (in this embodiment, the three-dimensional model of the rolled gauze 40) on the basis of the predetermined parameters to derive the surgical tool image E0. FIG. 7 is a diagram illustrating the derivation of the surgical tool image E0. As illustrated in FIG. 7, the derivation unit 32 projects a three-dimensional model 44 of the gauze onto a two-dimensional plane 46 in any line-of-sight direction 45 to derive the surgical tool image E0. In addition, the background of the surgical tool image E0 may have a predetermined density. For example, the intermediate value of the densities that can be taken by a radiographic image or the average density of a plurality of radiographic images may be used.

In addition, the derivation unit 32 sets parameters according to at least one of the contrast of the surgical tool in the surgical tool image E0 to be derived, the density of the surgical tool in the surgical tool image E0, or the noise included in the surgical tool image E0.

Here, in a case in which the radiation absorptivity of the surgical tool is high, the contrast of the surgical tool is high in the radiographic image acquired by performing radiography on the surgical tool (hereinafter, referred to as a surgical tool radiographic image). For example, in a case in which the surgical tool is a metal tool, such as a suture needle, scissors or a scalpel, the contrast of the surgical tool is higher than the contrast of the radiation absorbing thread 41 in the surgical tool radiographic image. That is, in the surgical tool radiographic image, a density difference between the background and the surgical tool is large. Therefore, the derivation unit 32 sets the density difference between the background and the surgical tool as a parameter such that the surgical tool image E0 having a contrast corresponding to the radiation absorptivity is derived. Then, the derivation unit 32 two-dimensionally projects the three-dimensional model of the surgical tool on the basis of the set parameter to derive the surgical tool image E0. Therefore, the surgical tool image E0 having the contrast based on the set parameter is derived.

In addition, the contrast of the radiographic image is reduced due to the scattering of radiation by the subject. The influence of the scattering of radiation becomes larger as the body thickness of the subject becomes larger. In addition, as the body thickness of the subject H becomes larger, the density of a subject region included in the radiographic image becomes lower. Therefore, the radiographic image has a density corresponding to the body thickness of the subject.

Here, beam hardening occurs in which, as the tube voltage applied to the radiation source 4 becomes higher and the energy of radiation becomes higher, a lower-energy component of the radiation is absorbed by the subject H and the energy of the radiation becomes higher while the radiation is transmitted through the subject H. In a case in which the beam hardening occurs, the contrast of the radiographic image decreases. Further, the increase in the energy of radiation due to the beam hardening becomes more significant as the body thickness of the subject H becomes larger. In addition, as the body thickness of the subject H becomes larger, the density of the subject region included in the radiographic image becomes lower.

Therefore, the derivation unit 32 sets the density of the surgical tool included in the surgical tool image E0 as a parameter such that the surgical tool included in the surgical tool image E0 has various densities. Then, the derivation unit 32 two-dimensionally projects the three-dimensional model of the surgical tool on the basis of the set parameter to derive the surgical tool image E0. Therefore, the surgical tool image E0 having the density based on the set parameter is derived.

In addition, in a case in which a radiation dose of the imaging conditions in the capture of the image of the subject H is reduced, the amount of noise included in the radiographic image increases. Therefore, in a case in which the three-dimensional model is two-dimensionally projected, the derivation unit 32 adds noise to derive the surgical tool image E0. In this case, the derivation unit 32 sets the amount of noise to be added as a parameter. Then, the derivation unit 32 two-dimensionally projects the three-dimensional model of the surgical tool on the basis of the set parameter to derive the surgical tool image E0. Therefore, the surgical tool image E0 having noise based on the set parameter is derived.

In addition, in this embodiment, various parameters may be prepared in advance and stored in the storage 13, and the derivation unit 32 may read each of the stored various parameters from the storage 13 and use the parameters to derive the surgical tool image E0. Further, a configuration may be used in which the user inputs the parameters with the input device 15 to set the parameters.

In this embodiment, the derivation unit 32 derives a plurality of surgical tool images E0 by two-dimensionally projecting the three-dimensional models of the gauzes 40 rolled by different methods in various directions or by changing the parameters in order to train the learning model which will be described below. In addition, the method for rolling the gauze 40, which is a three-dimensional model of the surgical tool, may be changed by displaying the three-dimensional model of the gauze on the display 14 and receiving an instruction from the input device 15.

Figure 8:
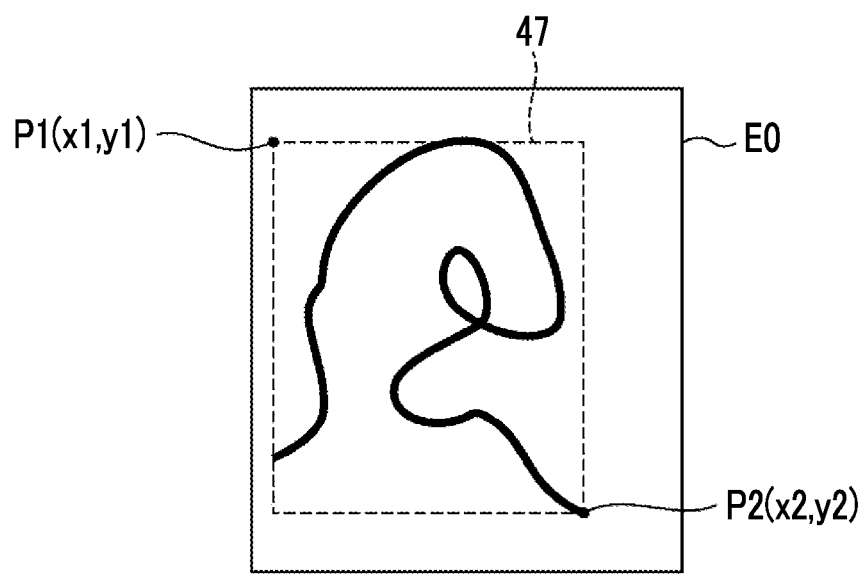
FIG. 8 is a diagram illustrating correct answer data in the surgical tool image.

The learning unit 33 trains the learning model M0, independently using each of the radiographic image G0 and the surgical tool image E0 as the training data. Here, as illustrated in FIG. 6, the surgical tool is not included over the entire surgical tool image E0. Therefore, in this embodiment, in a case in which the surgical tool image E0 is used as the training data, as illustrated in FIG. 8, the coordinates P1(x1, y1) of the upper left corner of a region 47 that surrounds the surgical tool in the surgical tool image E0 and the coordinates P2(x2, y2) of the lower right corner are used as correct answer data. In addition, the correct answer data may be the coordinates of the lower left corner and the upper right corner of the region 47 surrounding the surgical tool in the surgical tool image E0.

A machine learning model can be used as the learning model M0. One example of the machine learning model is a neural network model. Examples of the neural network model include a simple perceptron, a multilayer perceptron, a deep neural network, a convolutional neural network, a deep belief network, a recurrent neural network, and a stochastic neural network. In this embodiment, it is assumed that the convolutional neural network is used as the learning model M0.

Figure 9:
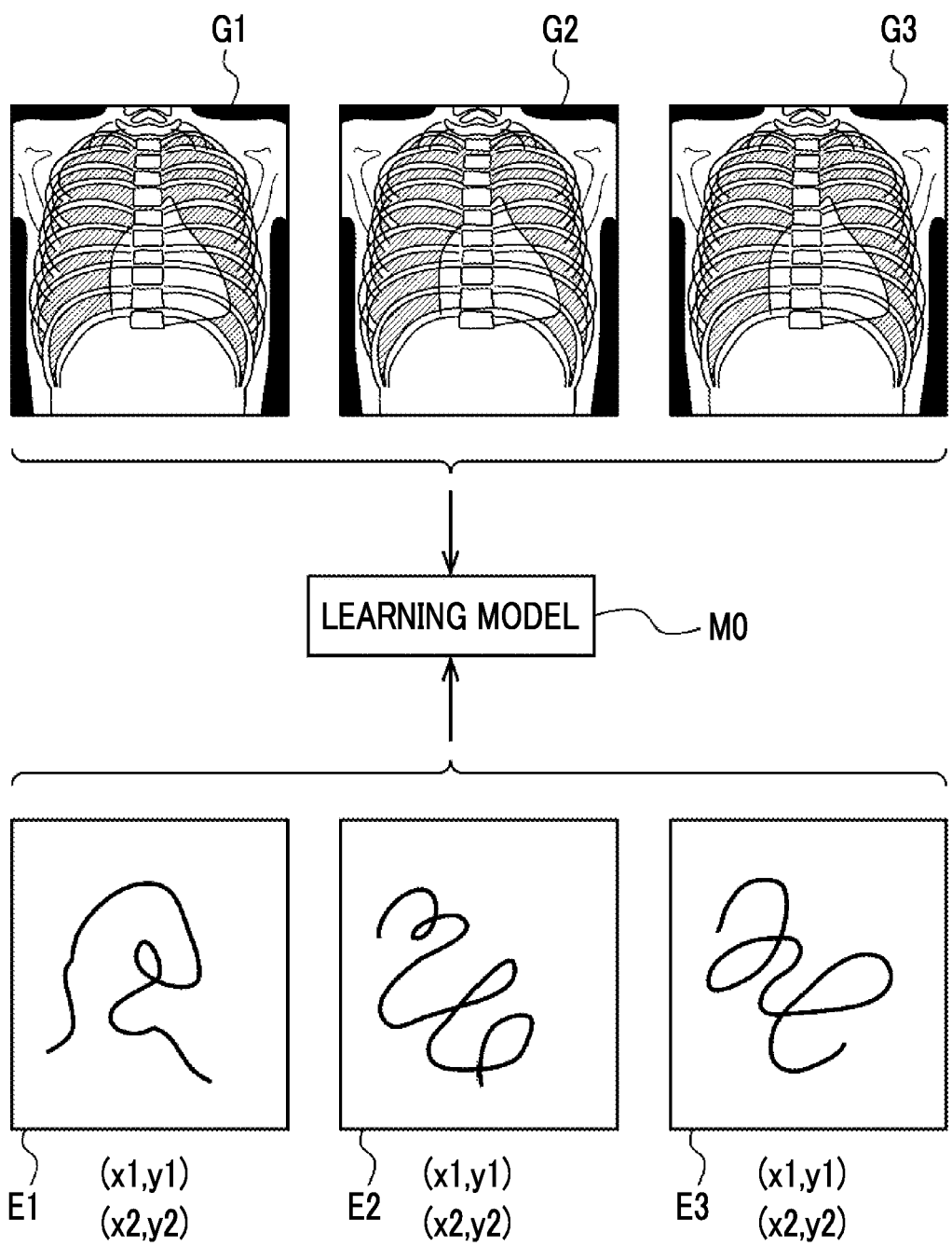
FIG. 9 is a diagram conceptually illustrating machine learning for a learning model.

FIG. 9 is a diagram conceptually illustrating the machine learning of the learning model M0 performed by the learning unit 33. In this embodiment, each of a plurality of radiographic images G0 (G1, G2, G3, . . . ) and a plurality of surgical tool images E0 (E1, E2, E3, . . . ) is used independently as the training data. That is, at the time of machine learning, each of the radiographic images G0 and the surgical tool images E0 is independently input to the learning model M0. In addition, for the surgical tool image E0, the training data includes correct answer data ((x1, y1), (x2, y2)) that defines the upper left corner and the lower right corner of the region of the surgical tool in the image.

In a case in which an image is input, the learning model M0 is trained so as to output the probability that each pixel of the image will be the region of the surgical tool. The probability is a value that is equal to or greater than 0 and equal to or less than 1. A region consisting of the pixels having the probability which has been output from the learning model M0 and is equal to or greater than a predetermined threshold value is the region of the surgical tool. The learning unit 33 inputs the training data to the learning model M0 and directs the learning model M0 to output the probability of each pixel being the region of the surgical tool. Then, the difference between the region consisting of the pixels having the probability which has been output from the learning model M0 and is equal to or greater than the predetermined threshold value and the region indicated by the correct answer data included in the training data is derived as a loss.

Here, in a case in which the radiographic image G0 is input as the training data to the learning model M0, the radiographic image G0 does not include the surgical tool. Therefore, the probability of each pixel being the region of the surgical tool has to be zero. However, the learning model M0 that has not been completely trained outputs a value greater than 0 as the probability of each pixel being the region of the surgical tool. Therefore, in a case in which the radiographic image G0 is input as the training data, the difference between the probability output for each pixel and 0 is a loss.

On the other hand, in a case in which the surgical tool image E0 is input as the training data to the learning model M0, the surgical tool image E0 includes the surgical tool. Therefore, the probability that each pixel in the region defined by the correct answer data in the surgical tool image E0 will be the region of the surgical tool has to be 1. However, the learning model M0 that has not been completely trained outputs a value less than 1 as the probability of each pixel being the region of the surgical tool. Therefore, in a case in which the surgical tool image E0 is input as the training data, the difference between the probability output for each pixel and 1 is a loss.

The learning unit 33 trains the learning model M0 on the basis of the loss. Specifically, for example, a kernel coefficient in the convolutional neural network and a weight for the connection of neural networks are derived so as to reduce the loss. The learning unit 33 repeats training until the loss is equal to or less than a predetermined threshold value. Therefore, a trained model M1 is constructed such that, in a case in which the radiographic image G0 is input, the probability that the entire image will be the region of the surgical tool approaches zero. Further, the trained model M1 is constructed such that, in a case in which the surgical tool image E0 is input, the probability that the region defined by the correct answer data will be the region of the surgical tool approaches 1. The constructed trained model M1 is stored in the memory 16.

In a case in which a radiographic image including the surgical tool is input to the trained model M1 constructed in this way, the trained model M1 outputs a probability close to 1 for the pixels in the region of the surgical tool in the radiographic image and outputs a probability close to 0 for the pixels in the other regions.

The detection unit 34 detects the region of the surgical tool from the target radiographic image T0 to be subjected to the surgical tool detection process using the trained model M1. Specifically, for each pixel of the target radiographic image T0, a region consisting of the pixels, for which the probability output from the trained model M1 is equal to or greater than a predetermined threshold value Th1, is detected as the region of the surgical tool. In addition, for all of the pixels of the target radiographic image T0, in a case in which the probability output from the trained model M1 is less than the threshold value Th1, the detection unit 34 outputs a detection result indicating that the target radiographic image T0 does not include the surgical tool.

Figure 10:
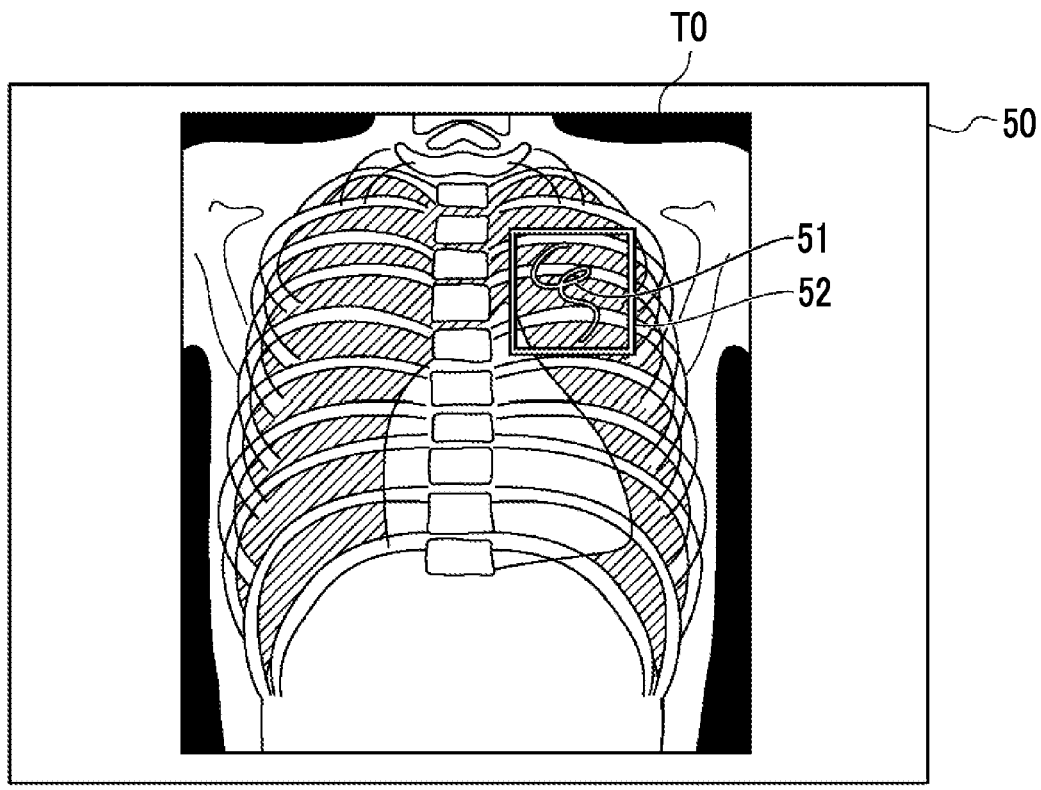
FIG. 10 is a diagram illustrating a target radiographic image display screen in a case in which the surgical tool is detected.

The display control unit 35 displays the target radiographic image T0 on the display 14 such that the region of the surgical tool detected from the target radiographic image T0 by the detection unit 34 is highlighted. FIG. 10 is a diagram illustrating a radiographic image display screen. As illustrated in FIG. 10, the target radiographic image T0 is displayed on a display screen 50, and a region 51 of the surgical tool included in the target radiographic image T0 is surrounded with a rectangular region 52 so as to be highlighted. In addition, the rectangular region 52 is illustrated in white in FIG. 10. However, the rectangular region 52 may be colored. Further, instead of giving the rectangular region 52, a mark, such as an arrow or an asterisk, may be given in the vicinity of the region of the surgical tool to highlight the region of the surgical tool. Further, the region 51 of the surgical tool may be masked to be highlighted. In addition, the mask may be colored.

In addition, in a case in which the target radiographic image T0 in which the region of the surgical tool has been highlighted is displayed, image processing for display, such as a gradation conversion process or a density conversion process, may be performed on the target radiographic image T0 in order to easily observe the target radiographic image T0. The display control unit 35 may perform the image processing for display, or an image processing unit for performing the image processing for display may be separately provided.

Figure 11:
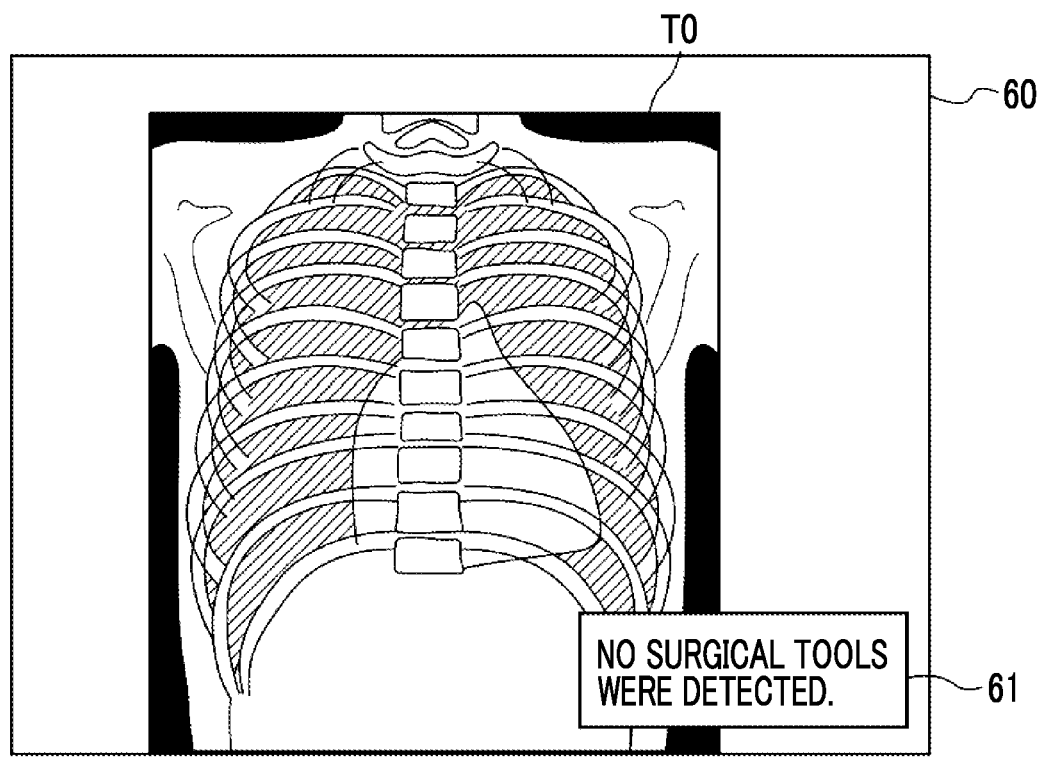
FIG. 11 is a diagram illustrating a target radiographic image display screen in a case in which the surgical tool is not detected.

In addition, in a case in which the detection unit 34 does not detect the region of the surgical tool from the target radiographic image T0, the display control unit 35 notifies the fact. FIG. 11 is a diagram illustrating a display screen of the target radiographic image T0 in a case in which the surgical tool is not detected. As illustrated in FIG. 11, a notification 61 of "No surgical tools were detected." is displayed on a display screen 60 so as to be superimposed on the target radiographic image T0. In addition, instead of the notification 61, for example, an icon or a mark indicating that no surgical tools were detected may be displayed. Further, the turn-on and turn-off of the display of the notification 61 may be switched by an instruction from the input device 15.

Figure 12:
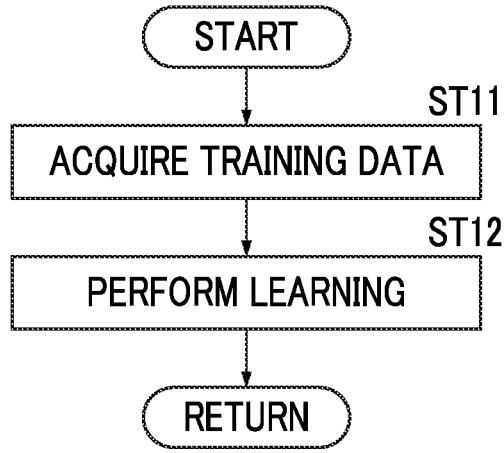
FIG. 12 is a flowchart illustrating a learning process according to this embodiment.

Next, a process performed in this embodiment will be described. FIG. 12 is a flowchart illustrating a learning process performed in this embodiment. The learning unit 33 acquires, as the training data, the radiographic image G0, the surgical tool image E0, and correct answer data defining the region of the surgical tool in the surgical tool image E0 (Step ST11). Then, the learning unit 33 trains the learning model M0 independently using each of the radiographic image G0 and the surgical tool image E0 as the training data (Step ST12) and returns to Step ST11. Then, the learning unit 33 repeats the process in Steps ST11 and ST12 until the loss reaches a predetermined threshold value and ends the training. In addition, the learning unit 33 may repeat the training a predetermined number of times and end the training. Therefore, the learning unit 33 constructs the trained model M1.

Figure 13:
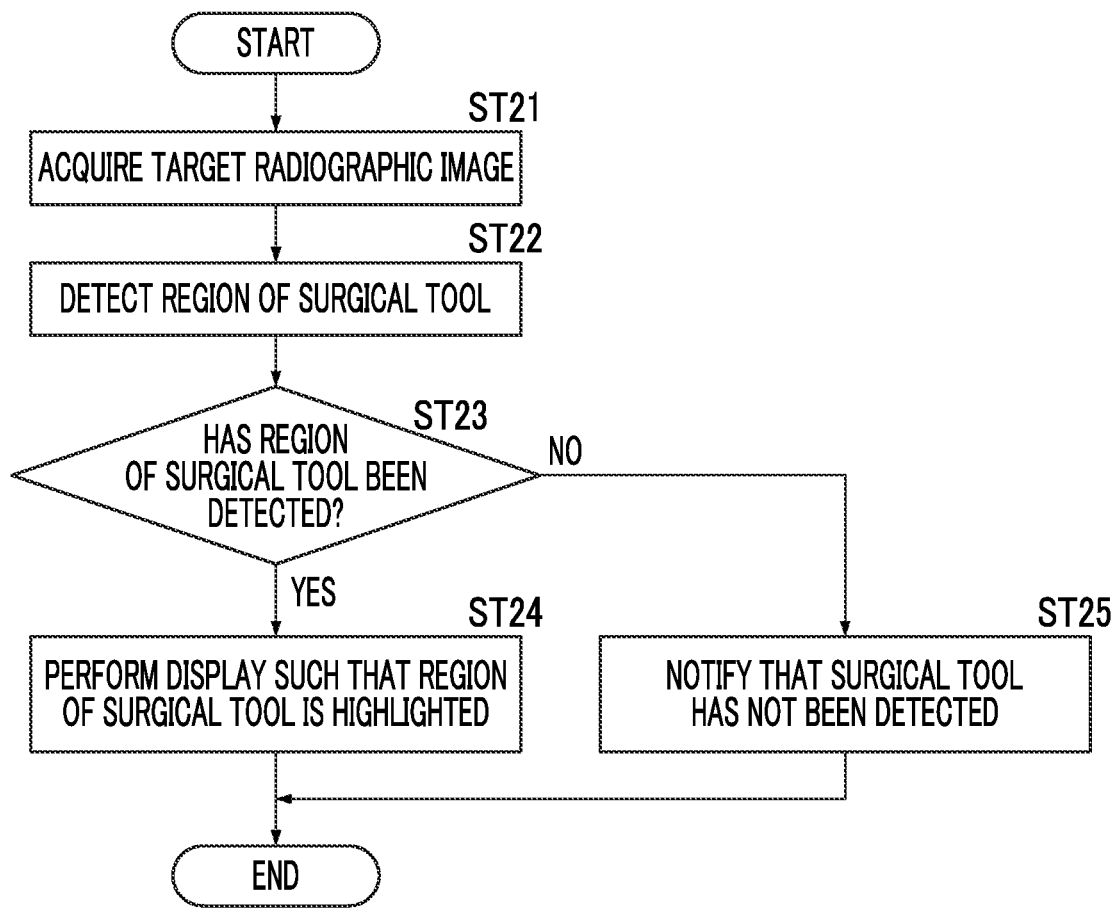
FIG. 13 is a flowchart illustrating a detection process according to this embodiment.

Next, a surgical tool region detection process according to this embodiment will be described. FIG. 13 is a flowchart illustrating the detection process performed in this embodiment. The image acquisition unit 31 acquires the target radiographic image T0 as a detection target (Step ST21), and the detection unit 34 detects the region of the surgical tool from the target radiographic image T0 using the trained model M1 (Step ST22). In a case in which the region of the surgical tool is detected from the target radiographic image T0 (Step ST23: YES), the display control unit 35 displays the target radiographic image T0 in which the region of the surgical tool has been highlighted on the display 14 (Step ST24). Then, the process ends. On the other hand, in a case in which the determination result in Step ST23 is "No", the display control unit 35 notifies that the region of the surgical tool has not been detected (Step ST25). Then, the process ends.

Here, since the radiographic image which includes the surgical tool and is necessary for training the learning model M0 is extremely rare, it is difficult to collect a large number of radiographic images for training the learning model M0. In this embodiment, the trained model M1 is constructed by performing machine learning which independently uses, as the training data, each of a plurality of radiographic images G0 that do not include the surgical tool and a plurality of surgical tool images E0 that include the surgical tool and have image quality corresponding to radiographic images. Therefore, since a sufficient amount of training data can be prepared, it is possible to sufficiently train the learning model M0. As a result, it is possible to construct the trained model M1 detecting the surgical tool with high accuracy.

In addition, since the radiographic image G0 is independently used as the training data, it is possible to train the learning model M0 without the structure of the subject H included in the radiographic image G0 being disturbed by the surgical tool, as compared to a case in which the radiographic image including the surgical tool is used as the training data. Further, since the surgical tool image E0 is independently used as the training data, it is possible to train the learning model M0 without the shape of the surgical tool being disturbed by the structure of the subject included in the radiographic image as compared to a case in which the radiographic image including the surgical tool is used as the training data. Therefore, it is possible to construct the trained model M1 with higher accuracy of detecting the surgical tool.

Further, in this embodiment, the trained model M1 constructed by performing machine learning, which independently uses each of the plurality of radiographic images G0 that do not include the surgical tool and the plurality of surgical tool images E0 as the training data, is used to detect the region of the surgical tool from the target radiographic image T0. Therefore, it is possible to detect the region of the surgical tool from the target radiographic image T0 with high accuracy. In addition, it is possible to reliably check whether or not the surgical tool remains in the body of the patient with reference to the detection result. As a result, according to this embodiment, it is possible to reliably prevent the surgical tool from remaining in the body of the patient after surgery.

In addition, the parameters in a case in which the three-dimensional model of the surgical tool is two-dimensionally projected according to at least one of the contrast of the surgical tool in the surgical tool image, the density of the surgical tool in the surgical tool image, or noise included in the surgical tool image are set. Therefore, the surgical tool image E0 acquired by a method other than radiography can have various image quality levels corresponding to radiographic images.

Further, in the above-described embodiment, gauze is detected as the surgical tool. However, the present disclosure is not limited thereto. Any surgical tool used in surgery, such as a scalpel, scissors, a drain, a suture needle, a thread, or forceps, can be detected. In this case, the surgical tool image E0 including the surgical tool may be derived by two-dimensionally projecting the three-dimensional model of the surgical tool on the basis of predetermined parameters. Further, the surgical tool image E0 may be acquired by performing radiography on a target surgical tool. Further, the learning unit 33 may perform machine learning for the learning model M0 so as to detect the target surgical tool. In addition, the learning model M0 may be trained to detect a plurality of channels, thereby constructing the trained model M1 so as to discriminate not only one kind of surgical tool but also a plurality of kinds of surgical tools.

In addition, in the above-described embodiment, the radiation is not particularly limited. For example, α-rays or γ-rays other than X-rays can be applied.

In the above-described embodiment, for example, the following various processors can be used as a hardware structure of processing units performing various processes, such as the image acquisition unit 31, the derivation unit 32, the learning unit 33, the detection unit 34, and the display control unit 35. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:
1. A learning device comprising:
at least one processor,
wherein the processor performs machine learning of a learning model by independently inputting each of a plurality of radiographic images that do not include a surgical tool and a plurality of surgical tool images that include only the surgical tool as training data to the learning model, to construct a trained model for detecting a region of the surgical tool from an input radiographic image, and
wherein the learning model comprises a neural network and the processor further performs the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

2. The learning device according to claim 1, wherein the surgical tool image is a radiographic image acquired by performing radiography only on the surgical tool.

3. The learning device according to claim 1, wherein the surgical tool image is acquired by a method other than the radiography and has an image quality corresponding to an image acquired by the radiography.

4. The learning device according to claim 3, wherein the processor two-dimensionally projects a three-dimensional model of the surgical tool on the basis of a predetermined parameter to derive the surgical tool image.

5. The learning device according to claim 4, wherein the processor sets the parameter according to at least one of a contrast of the surgical tool in the surgical tool image, a density of the surgical tool in the surgical tool image, or noise included in the surgical tool image.

6. The learning device according to claim 1, wherein the surgical tool includes at least one of gauze, a scalpel, scissors, a drain, a suture needle, a thread, or forceps.

7. The learning device according to claim 6, wherein the surgical tool comprises the gauze and at least a portion of the gauze includes a radiation absorbing thread.

8. A radiographic image processing device comprising:
at least one processor,
wherein the processor acquires a radiographic image and detects a region of a surgical tool from the radiographic image using a trained model constructed by a learning device,
wherein the learning device comprises at least one processor,
wherein the processor of the learning device performs machine learning of a learning model by independently inputting each of a plurality of radiographic images that do not include the surgical tool and a plurality of surgical tool images that include only the surgical tool as training data to the learning model, to construct the trained model for detecting the region of the surgical tool from the radiographic image, and
wherein the learning model comprises a neural network and the processor of the learning device further performs the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

9. A learning method comprising:
performing machine learning of a learning model by independently inputting each of a plurality of radiographic images that do not include a surgical tool and a plurality of surgical tool images that include only the surgical tool as training data to the learning model, to construct a trained model for detecting a region of the surgical tool from an input radiographic image, and
wherein the learning model comprises a neural network and the learning method further includes performing the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

10. A radiographic image processing method comprising:
acquiring a radiographic image; and
detecting a region of a surgical tool from the radiographic image using a trained model constructed by a learning device,
wherein the learning device comprises at least one processor,
wherein the processor of the learning device performs machine learning of a learning model by independently inputting each of a plurality of radiographic images that do not include the surgical tool and a plurality of surgical tool images that include only the surgical tool as training data to the learning model, to construct the trained model for detecting the region of the surgical tool from the radiographic image, and
wherein the learning model comprises a neural network and the processor of the learning device further performs the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

11. A non-transitory computer-readable storage medium that stores a learning program that causes a computer to perform: a procedure of performing machine learning of a learning model by independently inputting each of a plurality of radiographic images that do not include a surgical tool and a plurality of surgical tool images that include only the surgical tool as training data to the learning model, to construct a trained model for detecting a region of the surgical tool from an input radiographic image, and
wherein the learning model comprises a neural network and the learning program further causes the computer to perform the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

12. A non-transitory computer-readable storage medium that stores a radiographic image processing program that causes a computer to perform:
a procedure of acquiring a radiographic image; and
a procedure of detecting a region of a surgical tool from the radiographic image using a trained model constructed by a learning device,
wherein the learning device comprises at least one processor,
wherein the processor of the learning device performs machine learning of a learning model by independently inputting each of a plurality of radiographic images that do not include the surgical tool and a plurality of surgical tool images that include only the surgical tool as training data to the learning model, to construct the trained model for detecting the region of the surgical tool from the radiographic image, and
wherein the learning model comprises a neural network and the processor of the learning device further performs the machine learning of the neural network, in which when a radiographic image that does not include the surgical tool is input to the neural network as the training data, a probability of being the region of the surgical tool that is output from the neural network becomes 0 in an entire region of the input radiographic image that does not include the surgical tool, and when a surgical tool image is input to the neural network as the training data, the probability of being the region of the surgical tool that is output from the neural network becomes 1 in the region of the surgical tool in the input surgical tool image.

* * * * *